(12) United States Patent
Nield et al.

(10) Patent No.: US 7,063,695 B2
(45) Date of Patent: *Jun. 20, 2006

(54) OPTICAL FIBER FOR A LASER DEVICE HAVING AN IMPROVED DIFFUSER SLUG AND METHOD OF MAKING SAME

(75) Inventors: Scott A. Nield, Cincinnati, OH (US); Jane A. Sheetz, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 147 days.

This patent is subject to a terminal disclaimer.

(21) Appl. No.: 10/741,454

(22) Filed: Dec. 19, 2003

(65) Prior Publication Data

US 2005/0137587 A1 Jun. 23, 2005

(51) Int. Cl.
*A61B 18/22* (2006.01)
(52) U.S. Cl. .......................... 606/15; 385/123; 606/13
(58) Field of Classification Search ............ 606/13–16; 385/123
See application file for complete search history.

(56) References Cited

U.S. PATENT DOCUMENTS

| | | |
|---|---|---|
| 4,476,512 A | 10/1984 | Sunago et al. |
| 4,695,697 A | 9/1987 | Kosa |
| 4,708,494 A | 11/1987 | Kleinerman |
| 4,822,997 A | 4/1989 | Fuller et al. |
| 5,004,913 A | 4/1991 | Kleinerman |
| 5,057,099 A | 10/1991 | Rink |
| 5,074,632 A | 12/1991 | Potter |
| 5,154,707 A | 10/1992 | Rink et al. |
| 5,196,005 A | 3/1993 | Doiron et al. |
| 5,267,995 A | 12/1993 | Doiron et al. |
| 5,269,777 A | 12/1993 | Doiron et al. |
| 5,303,324 A | 4/1994 | Lundahl |

(Continued)

FOREIGN PATENT DOCUMENTS

DE 41 37 983 A1 6/1992

(Continued)

OTHER PUBLICATIONS

EPO Search Report dated Mar. 11, 2005 for corresponding patent application, European Patent Application No. EP 04 25 7932.

(Continued)

*Primary Examiner*—Lee S Cohen
*Assistant Examiner*—Henry M Johnson, III

(57) ABSTRACT

An optical fiber for use with a laser device including a source of light energy, as well as a method of making such optical fiber, where the optical fiber has a proximal end in communication with the light source and a diffuser portion positionable at a treatment site. The optical fiber includes: a core having a proximal portion, a distal portion and a distal face proximate the diffuser portion of the optical fiber; a layer of cladding radially surrounding the core from the core proximal portion to a point adjacent the core distal portion; a layer of optical coupling material radially surrounding at least a portion of the core distal portion; a slug including a light-scattering material therein positioned adjacent the distal face of the core and a distal end of the optical coupling layer, wherein the light-scattering material fluoresces in a temperature dependent manner upon being stimulated by light; and, a sleeve radially surrounding the cladding layer, the optical coupling layer and the slug, wherein the sleeve is composed essentially of a predetermined type of material; wherein the light-scattering material of the slug is molded with substantially the same type of material utilized for the sleeve.

14 Claims, 7 Drawing Sheets

U.S. PATENT DOCUMENTS

| | | |
|---|---|---|
| 5,337,381 A | 8/1994 | Biswas et al. |
| 5,363,458 A | 11/1994 | Pan et al. |
| 5,383,874 A | 1/1995 | Jackson et al. |
| 5,400,267 A | 3/1995 | Denen et al. |
| 5,401,270 A * | 3/1995 | Muller et al. .................. 606/13 |
| 5,431,647 A * | 7/1995 | Purcell et al. ................. 606/16 |
| 5,469,524 A | 11/1995 | Esch et al. |
| 5,487,386 A | 1/1996 | Wakabayashi et al. |
| 5,493,629 A | 2/1996 | Stange |
| 5,651,780 A | 7/1997 | Jackson et al. |
| 5,749,871 A | 5/1998 | Hood et al. |
| 5,754,717 A | 5/1998 | Esch |
| 5,802,229 A | 9/1998 | Evans et al. |
| 5,848,209 A | 12/1998 | Evans et al. |
| 5,875,275 A | 2/1999 | Evans et al. |
| 5,908,415 A | 6/1999 | Sinofsky |
| 5,945,667 A | 8/1999 | Bohnert et al. |
| 5,946,441 A | 8/1999 | Esch |
| 5,978,541 A | 11/1999 | Doiron et al. |
| 5,991,355 A | 11/1999 | Dahlke |
| RE36,473 E | 12/1999 | Esch et al. |
| 6,237,604 B1 | 5/2001 | Burnside et al. |
| 6,240,225 B1 | 5/2001 | Prohaska |
| 6,361,530 B1 | 3/2002 | Mersch |
| 6,370,310 B1 | 4/2002 | Jin et al. |
| 6,387,092 B1 | 5/2002 | Burnside et al. |
| 6,464,689 B1 | 10/2002 | Qin et al. |
| 6,503,269 B1 | 1/2003 | Nield et al. |
| 6,522,806 B1 | 2/2003 | James, IV et al. |
| 6,562,028 B1 | 5/2003 | Nield et al. |
| 6,576,163 B1 * | 6/2003 | Mersch ....................... 264/1.1 |
| 6,718,089 B1 * | 4/2004 | James et al. .................. 385/31 |
| 2001/0025173 A1 | 9/2001 | Ritchie et al. |
| 2002/0045922 A1 | 4/2002 | Nield et al. |
| 2002/0049435 A1 * | 4/2002 | Mersch ....................... 606/15 |
| 2002/0081871 A1 | 6/2002 | Swayze et al. |
| 2002/0120262 A1 | 8/2002 | Bek et al. |
| 2002/0198519 A1 | 12/2002 | Qin et al. |
| 2003/0118302 A1 | 6/2003 | James, IV et al. |
| 2005/0094947 A1 * | 5/2005 | James et al. .................. 385/88 |
| 2005/0135749 A1 * | 6/2005 | Nield et al. .................... 385/38 |
| 2005/0135772 A1 * | 6/2005 | Nield et al. .................. 385/140 |

FOREIGN PATENT DOCUMENTS

| | | |
|---|---|---|
| EP | 0 951 921 A3 | 3/2000 |
| WO | WO 92/17243 A2 | 10/1992 |
| WO | WO 02/35264 A1 | 5/2002 |

OTHER PUBLICATIONS

Mizeret J C et al: "Cylindrical Fiberoptic Light Diffuser for Medical Applications", Lasers in Surgery and Medicine, 1996, pp. 159-167, vol. 19, No. 2, Wiley-Liss, Inc., New York, U.S.

* cited by examiner

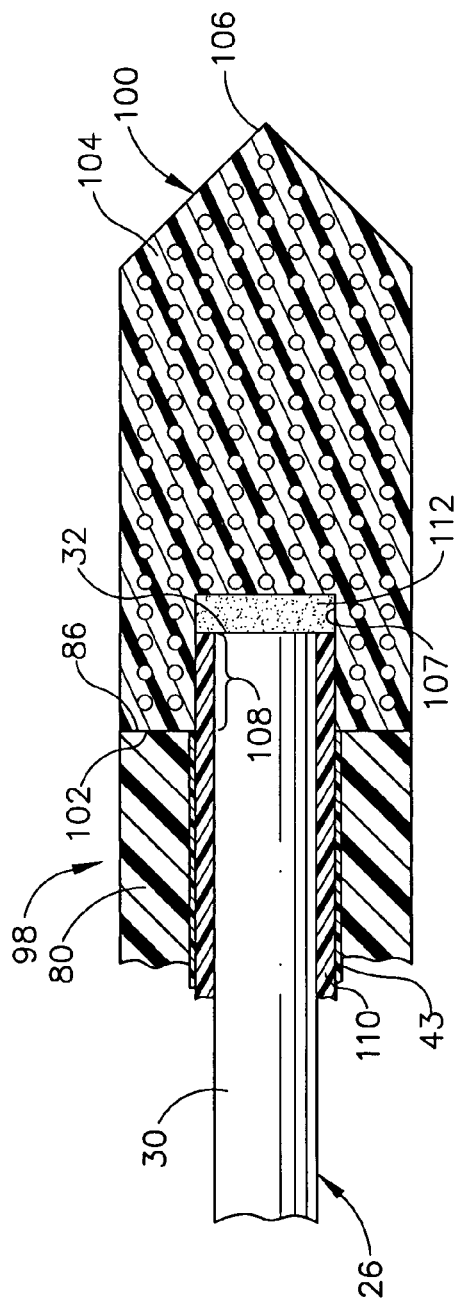
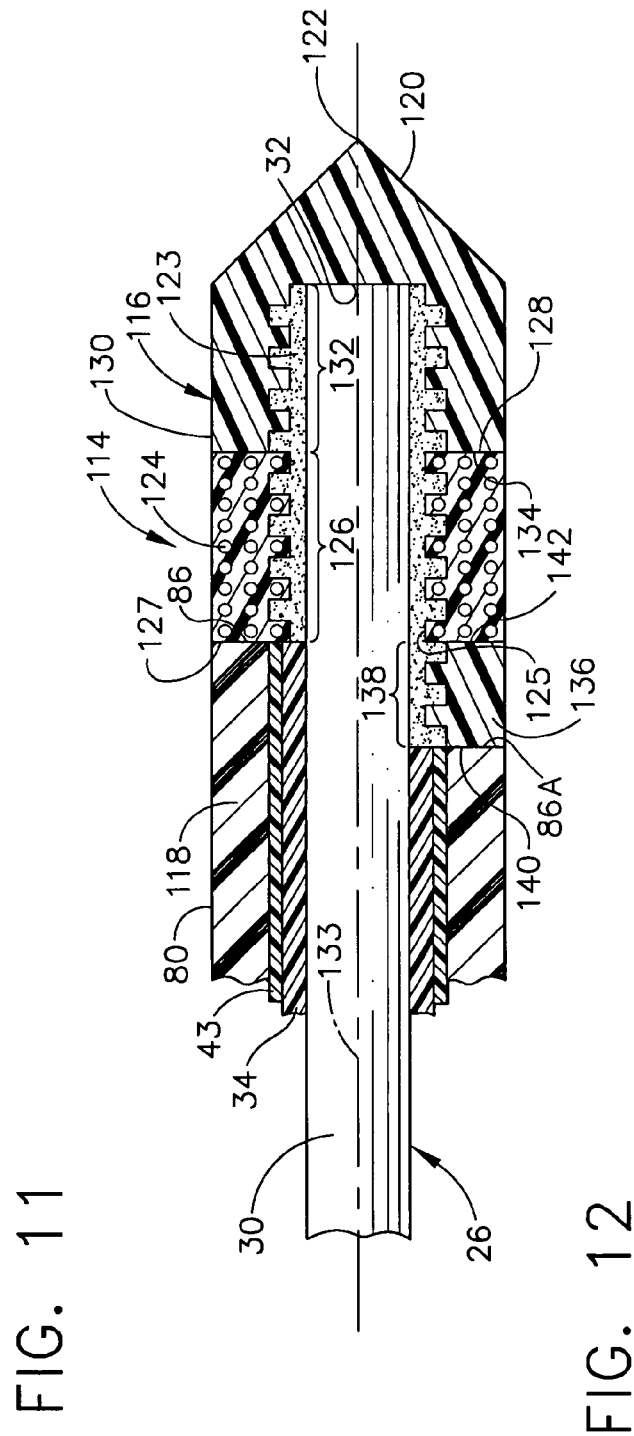
FIG. 11
FIG. 12

OPTICAL FIBER FOR A LASER DEVICE HAVING AN IMPROVED DIFFUSER SLUG AND METHOD OF MAKING SAME

RELATED APPLICATIONS

This patent application cross references and incorporates by reference the following copending, commonly assigned patent applications filed on even date herewith: "OPTICAL FIBER FOR A LASER DEVICE HAVING AN IMPROVED TIP DIFFUSER AND METHOD OF MAKING SAME", U.S. Ser. No. 10/741,609; and "OPTICAL FIBER TIP DIFFUSER AND METHOD OF MAKING SAME", U.S. Ser. No. 10/741,393.

BACKGROUND OF THE INVENTION

The present invention relates generally to an optical fiber for use with a laser device and, more particularly, to an optical fiber having an improved diffuser configuration at its distal end for performing the dual functions of scattering light and providing a temperature signal.

Currently, surgeons employ medical instruments which incorporate laser technology in the treatment of benign prostatic hyperplasia, also commonly referred to as BPH. BPH is a condition of an enlarged prostate gland, where such gland having BPH typically increases in size to by about two to four times. The laser energy employed by the surgeons to treat this condition is delivered by an optical fiber which must be able to distribute light radially in a predictable and controlled manner. During the course of such treatments, one parameter of great importance is the temperature of the tissue being treated. For example, one current recommendation for forming lesions in the prostate as a treatment for BPH is to heat a small volume of tissue to 85° C. for a designated time period depending on fiber and laser design. It will be appreciated that heating the tissue to a lesser temperature has the effect of incomplete lesion formation, while heating the tissue to a higher temperature can cause excessive tissue damage. Accordingly, the ability to accurately measure the temperature of the optical fiber tip during treatment is of primary concern.

It will be understood that there are several known ways of performing the temperature monitoring function for a laser system. One approach has been utilized in laser treatment systems known as the "Indigo 830e Laseroptic Treatment System" and the "Indigo Optima Laseroptic Treatment System," both of which are manufactured by Ethicon EndoSurgery, Inc. of Cincinnati, Ohio, the assignee of the present invention. Methods of providing an optical fiber with a diffuser end are disclosed in U.S. Pat. No. 6,522,806 to James, IV et al., U.S. Pat. No. 6,361,530 to Mersch, and U.S. Pat. No. 5,946,441 to Esch. Each of these methods utilize the principle of relying upon the temperature dependence of the fluorescent response of a slug of material at the fiber tip to an optical stimulus as described in U.S. Pat. Nos. 5,004,913 and 4,708494 to Kleinerman. More specifically, a pulse of pump energy causes a fluorescence pulse in an alexandrite slug which is delayed by a time interval corresponding to a temperature of the material.

It will be appreciated from each of the aforementioned patents that the slug is composed of a cured mixture of alexandrite particles and an optical adhesive which is cured in place. The current manufacture and assembly of such slugs is considered both complex and tedious. In an exemplary process, the slugs are formed in batches by sprinkling ground alexandrite into several tiny cavities in a mold placed on a vibratory plate. The alexandrite particles are then covered with an optical coupling adhesive, after which a vacuum is drawn and the mixture is cured within the mold using either heat or ultraviolet light. The slugs are removed from the mold as a batch and placed individually into the distal sleeve tip against the end of the fiber optic glass during assembly.

While various improvements have been made in the basic slug manufacturing process, they are all based on the slug being a mixture of alexandrite and adhesive and therefore have similar disadvantages. One disadvantage is that a portion of the final molded configuration is used as structural support, which results in substantial waste of the expensive alexandrite material. The manufacturing process is considered to be lengthy and requires the use of specialized equipment and highly trained operators. Moreover, the ratio of alexandrite to the ultraviolet binder (i.e., its concentration) in each individual cavity of the slug mold is not precisely controlled, which results in a variation of the slug composition and its resulting performance. It will also be understood that assembly of the slug within the distal tip of the optical fiber is difficult since the slug is unidirectional, the size of the components in the optical fiber is extremely small, direct visualization is not available, and neither mechanical positioning nor final mechanical interlock is provided between the components.

In an alternate variation of the current manufacturing process, an uncured mixture of alexandrite and adhesive may be directly applied to the end of the fiber and cured into place. This may be accomplished by dispensing the mixture within the tubing directly onto the end of the glass core, loading it into a sleeve or other carrier and seating the sleeve, or by dipping the core end into adhesive and then into the alexandrite particles. It has been found in this process, however, that application of a consistent amount of the mixture in the proper location is difficult to achieve and monitor on a production basis.

Thus, in light of the foregoing, it would be desirable for a slug, as well as a method of making and assembling such slug in an optical fiber, to be developed which overcomes the disadvantages associated with the alexandrite and adhesive composition and manufacturing processes described herein. It is also desirable that such slug would assist in centering the slug on the distal surface of the optical fiber and assuring contact between the core fiber and an outer sleeve, whereby the dual functions of light scattering and temperature sensing are optimized. Further, it is highly desirable for the light-scattering material and the sleeve of the diffuser portion for such optical fiber to be formed in an integral manner. In an alternative configuration, it would be desirable for the separate slug to be eliminated from the optical fiber and replaced with a tip diffuser having light scattering and temperature sensing capabilities which can be assembled to the distal end of the optical fiber.

BRIEF SUMMARY OF THE INVENTION

In a first exemplary embodiment of the invention, an optical fiber is disclosed for use with a laser device including a source of light energy, where the optical fiber has a proximal end in communication with the light source and a diffuser portion positionable at a treatment site. The optical fiber includes: a core having a proximal portion, a distal portion and a distal face proximate the diffuser portion of the optical fiber; a layer of cladding radially surrounding the core from the core proximal portion to a point adjacent the core distal portion; a layer of optical coupling material radially surrounding at least a portion of the core distal portion; a slug including a light-scattering material therein positioned adjacent the distal face of the core and a distal end of the optical coupling layer, wherein the light-scattering material fluoresces in a temperature dependent manner upon being stimulated by light; and, a sleeve radially surrounding the cladding layer, the optical coupling layer and the slug, wherein the sleeve is composed essentially of a predetermined type of material; wherein the light-scattering material of the slug is molded with substantially the same type of material utilized for the sleeve.

In a second exemplary embodiment of the invention, a method of making an improved diffuser portion of an optical fiber for use with a laser device is disclosed, wherein the optical fiber includes a core having a proximal portion, a distal portion, and a distal surface. The method includes the following steps: providing a sleeve radially around the core so that a length of the open sleeve extends beyond the core distal portion a predetermined amount, wherein the sleeve is essentially composed of a predetermined type of material; molding a light-scattering material with the same type of material as the sleeve to form a slug, wherein the light-scattering material fluoresces in a temperature dependent manner upon being stimulated by light; inserting the slug into the open sleeve length so as to be positioned adjacent the distal face of the core; and, shaping the open sleeve length into a penetrating tip having a predetermined geometry.

BRIEF DESCRIPTION OF THE DRAWINGS

FIG. 11 is an enlarged, partial sectional view of a second alternative embodiment for the optical fiber depicted in FIGS. 1–3, where a tip diffuser is in the attached position and the penetrating tip has been formed;

FIG. 12 is an enlarged, partial sectional view of a fourth alternative embodiment for the optical fiber depicted in FIGS. 1–3, where a tip diffuser including a ring-shaped portion made of light scattering material and the sleeve material is in the attached position and the penetrating tip has been formed; and, FIG. 13 is an enlarged, partial sectional view of a third alternative embodiment for the optical fiber depicted in FIGS. 1–3, where a tip diffuser incorporating a ring-shaped slug made of light scattering material is in the attached position and the penetrating tip has been formed.

DETAILED DESCRIPTION OF THE INVENTION

Figure 1:
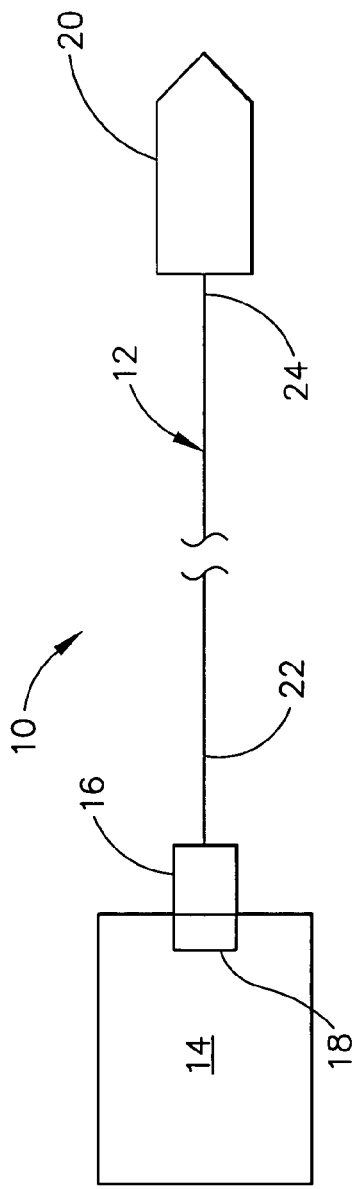
FIG. 1 is a diagrammatic view of a laser system utilized for performing medical procedures which includes the optical fiber of the present invention.

Referring now to the drawings in detail, wherein identical numerals indicate the same elements throughout the figures, FIG. 1 depicts schematically a medical instrument 10 for diffusing light from an optical fiber 12. Medical instrument 10 includes a source of light energy 14, which preferably is a laser. Optical fiber 12 connects into light energy source 14 through the intermediary of a connector 16 which is attached to a connection port 18 leading to a diffuser portion 20 of optical fiber 12. A typical connector and connection port of this kind which can be utilized for medical instrument 10 is the Optima laser which is sold by Ethicon Endo-Surgery in Cincinnati, Ohio. It will be appreciated that optical fiber 12 with the attached connector 16 may be provided and sold separately from light energy source 14 as an optic fiber assembly.

More specifically, optical fiber 12 includes a proximal end 22 in communication with light energy source 14 which transmits light to a distal end 24 including diffuser portion 20 that is utilized to diffuse light at a treatment site. Optical fiber 12 further includes a plurality of assembled components which enable it to function in an intended manner, as in the case for the treatment of BPH. It will be seen from FIGS. 2 and 3 that optical fiber 12 includes a core 26 which extends substantially through the center of optical fiber 12. Core 26, which is typically made of silica glass, has a proximal portion 28 in communication with light energy source 14 and functions to transmit light to a distal portion 30 that is located within diffuser portion 20. It will be understood that distal portion 30 includes a distal face 32. In this way, diffuser portion 20 functions to diffuse the light energy received from proximal portion 28. A layer of cladding 34 is preferably provided so as to radially surround core 26 from core proximal portion 28 to a point adjacent to core distal portion 30. Cladding layer 34, which protects core 26 by imparting a mechanical support thereto, preferably has an index of refraction lower than that of the material used to create core 26 so as to contain or block the light transmitted through optical fiber 12 from emerging radially from core 26.

Optical fiber 12 further includes a layer 36 of optical coupling material which preferably radially surrounds at least a portion 38 of core distal portion 30 and possibly a portion of cladding layer 34. Exemplary optical coupling materials include: XE5844 Silicone, which is made by General Electric Company; UV50 Adhesive, available from Chemence, Incorporated in Alpharetta, Ga.; and, 144-M medical adhesive, which is available from Dymax of Torrington, Conn. Optical coupling layer 36 preferably has a higher index of refraction than core 26 so that light exits core 26.

Figure 2:
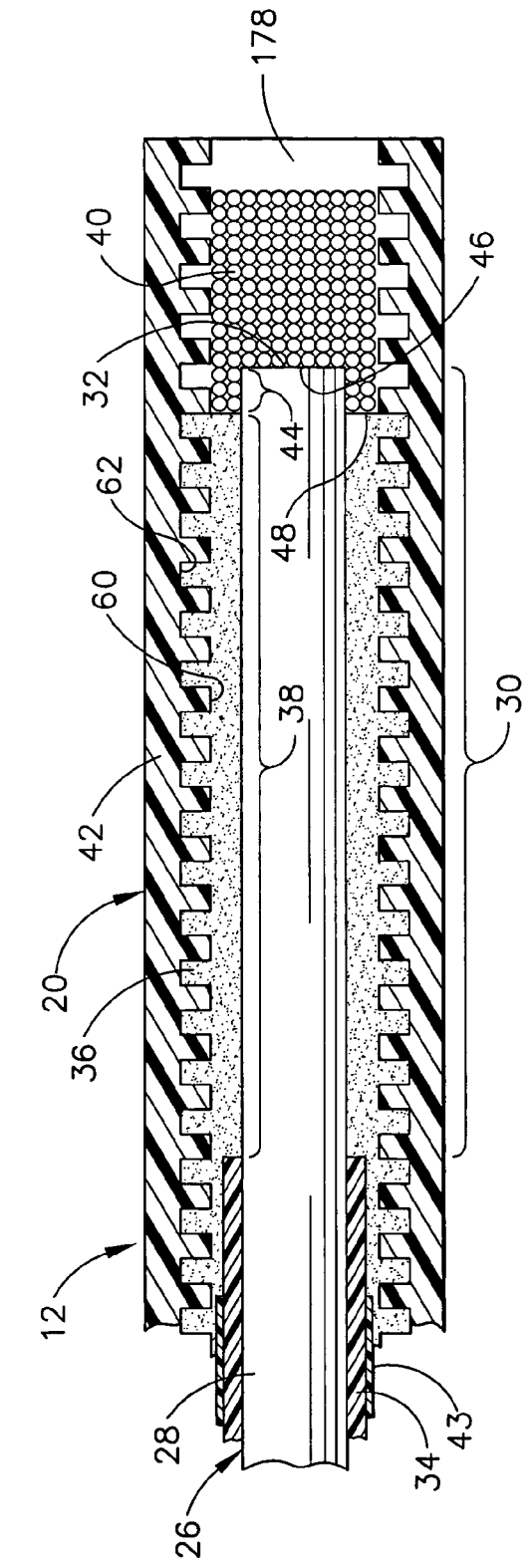
FIG. 2 is an enlarged, partial sectional view of the optical fiber depicted in FIG. 1, where the penetrating tip has not been formed.
Figure 3:
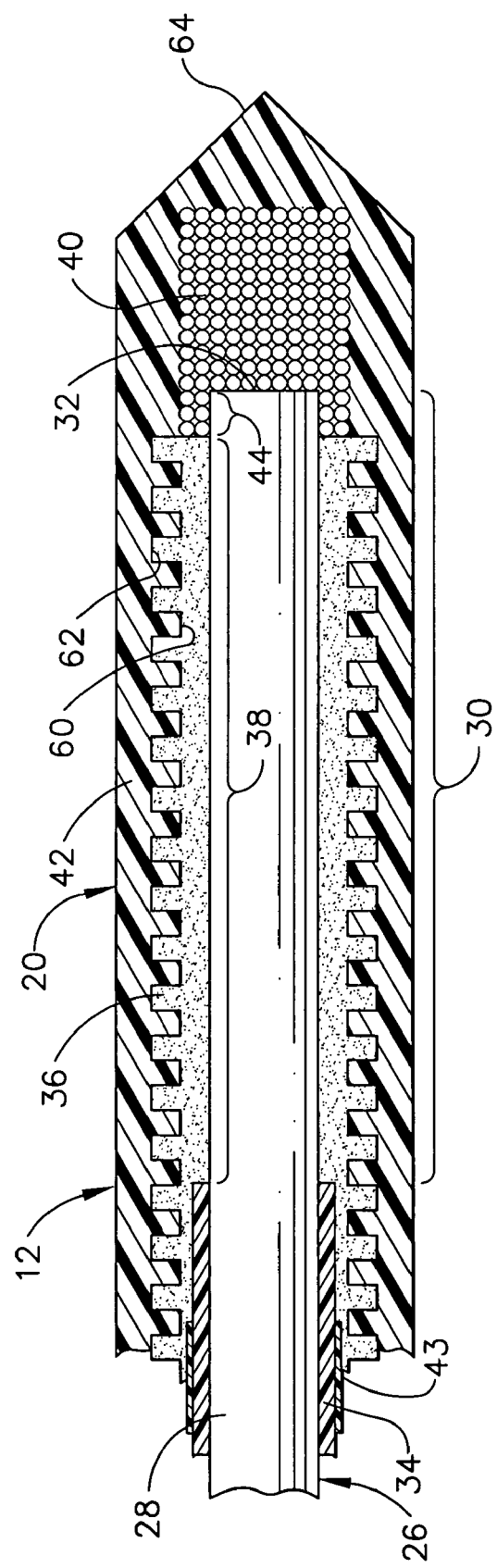
FIG. 3 is an enlarged, partial sectional view of the optical fiber depicted in FIGS. 1 and 2, where the penetrating tip has been formed.

In the embodiment of the invention depicted in FIGS. 2 and 3, a slug 40 positioned adjacent distal face 32 functions to scatter light back through core 26 and thereby raise the intensity of the light in diffuser portion 20. Slug 40, as discussed previously herein, has heretofore been composed essentially of a light-scattering material and an adhesive. Typical scattering materials have included aluminum oxide, titanium dioxide, and diamond power, but alexandrite has been found to be a preferred material. This is because alexandrite not only is able to perform the light-scattering function, but it also exhibits a temperature dependent optical fluorescence decay rate upon being stimulated by light of a predetermined wavelength. Accordingly, the alexandrite is able to emit a light signal back through core 26 from which a temperature for diffuser portion 20 can be determined and controlled. It will be appreciated that the adhesive generally mixed with the light-scattering material may or may not be the same as for optical coupling layer 36.

It will be noted that optical fiber 12 also preferably includes a sleeve 42 which radially surrounds optical coupling layer 36 and slug 40. A buffer layer 43 is preferably positioned radially between sleeve 42 and cladding layer 34 upstream of and perhaps into diffuser portion 20. Sleeve 42 is composed essentially of a predetermined type of material which preferably has an index of refraction higher than the material used for optical coupling layer 36. Further, such material is preferably flexible, is non-absorbent of laser energy in the wavelengths of interest, has a high melt temperature, and is optically diffusing. A preferred material for sleeve 42 having the desired characteristics is perfluoroalkoxy (PFA) impregnated with barium sulfate, where the barium sulfate particles assist in scattering light energy evenly outward to the tissue at the treatment site. Other materials optically transparent to the appropriate wavelengths may be used to construct sleeve 42, including Ethylenetetraflouroethylene (ETFE) and other types of flouropolymers.

Turning back to slug 40, the present invention involves molding the alexandrite (or other light-scattering material having similar temperature dependent properties when stimulated by light) with substantially the same type of material utilized for sleeve 42. It will be appreciated that a preferred concentration of the alexandrite in slug 40 exists and is dependent upon the configuration and composition of slug 40. In the case where slug 40 is a substantially homogeneous mixture of alexandrite and perfluoroalkoxy with approximately 10% barium sulfate (see FIG. 4), the preferred concentration of alexandrite therein is in a range of approximately 25–75% by weight.

Figure 7:
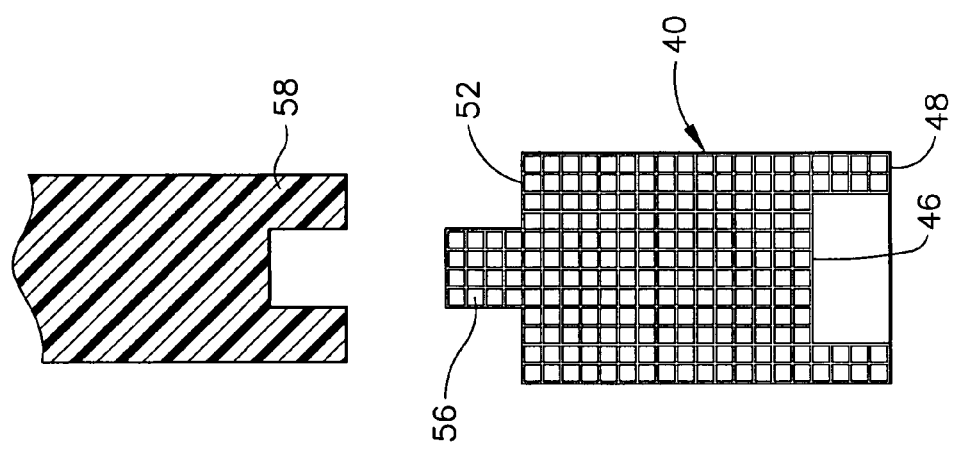
FIG. 7 is an enlarged, sectional view of the slug depicted in FIG. 4 including a feature formed in one end thereof for interfacing with an assembly tooling spaced therefrom.
Figure 8:
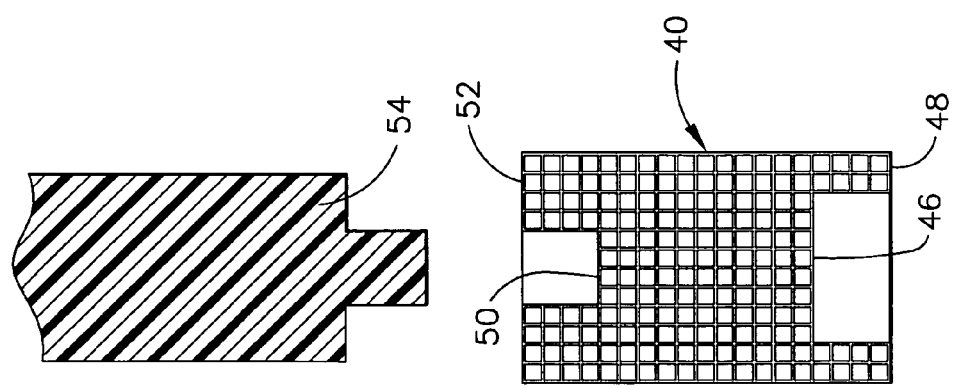
FIG. 8 is an enlarged, sectional view of the slug depicted in FIG. 4 including an alternative feature formed in one end thereof for interfacing with an assembly tooling spaced therefrom.

With respect to the overall configuration of slug 40, it will be seen that slug 40 preferably radially surrounds a portion 44 of core distal portion 30. Accordingly, a feature 46 is preferably incorporated into a first end 48 of slug 40 for centering slug 40 onto core distal portion 30. Further, slug 40 preferably includes a negative feature 50 formed into a second end 52 thereof for interfacing with a positive assembly tooling 54 (see FIG. 7). Alternatively, a positive feature 56 is preferably formed into second end 52 thereof for interfacing with a negative assembly tooling 58 (see FIG. 8). In either case, insertion of slug 40 onto core distal portion 30 is facilitated. It will be appreciated, however, that differing the tooling feature from the centering feature assists in preventing misassembly. Because slug 40 essentially consists of the same type of material as that utilized for sleeve 42, and an interior surface 60 of sleeve 42 is preferably abraded to include grooves 62 or other variable surface characteristics, slug 40 achieves a mechanical connection with sleeve 42 via a physical bonding during the formation of a penetrating tip 64 on sleeve 42. In particular, the material of slug 40 melts and bonds with the material of sleeve 42 since they have substantially the same melting points.

Figure 6:
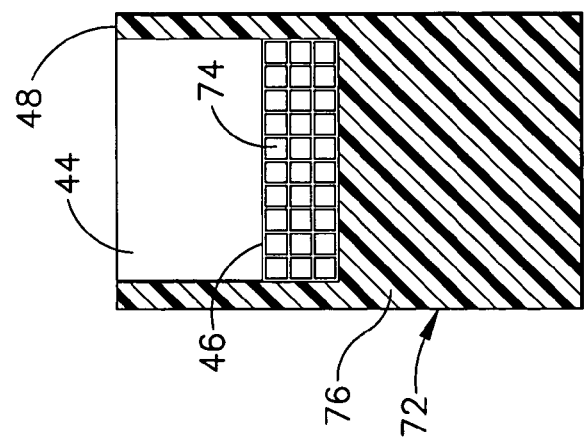
FIG. 6 is an enlarged, sectional view of a second alternative embodiment for the slug depicted in FIGS. 2 and 3.
Figure 5:
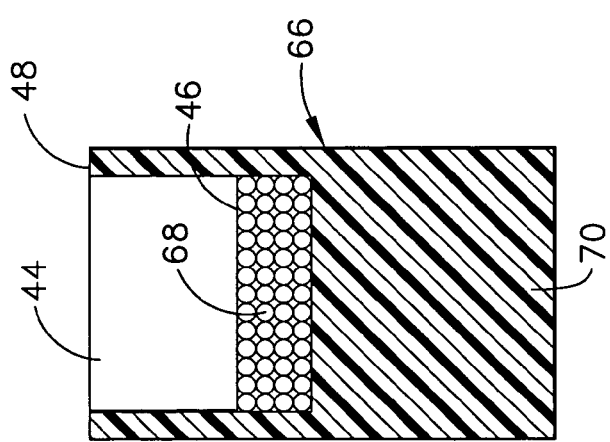
FIG. 5 is an enlarged, sectional view of a first alternative embodiment for the slug depicted in FIGS. 2 and 3.
Figure 4:
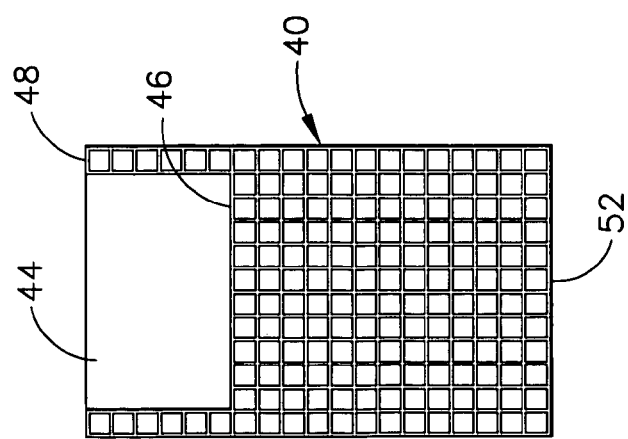
FIG. 4 is an enlarged, sectional view of the slug in the optical fiber as depicted in FIGS. 2 and 3.

It will also be seen that additional embodiments of slug 40 are depicted in FIGS. 5 and 6 which differ from the substantially homogeneous mixture represented in FIG. 4. In FIG. 5, slug 66 includes a first portion 68 consisting essentially of a light-scattering material (e.g., alexandrite or any other material having similar properties and characteristics) which is positioned adjacent to core distal face 32. In addition, slug 66 includes a second portion 70 consisting essentially of the same type of material utilized for sleeve 42 (e.g., perfluoroalkoxy with barium sulfate particles or any other material having similar properties and characteristics). Second slug portion 70 is preferably molded so as to be positioned around first slug portion 68 and portion 44 of core distal portion 30.

With respect to FIG. 6, it will be seen that slug 72 therein includes a first portion 74 consisting essentially of a substantially homogeneous mixture of a light-scattering material and material of the same type utilized for sleeve 42 (e.g., alexandrite and perfluoroalkoxy with barium sulfate particles or other compositions having similar properties and characteristics), where first slug portion 74 is positioned adjacent to core distal face 32. A second portion 76 of slug 72 consisting essentially of the same type of material utilized for sleeve 42 (e.g., perfluoroalkoxy with barium sulfate particles or any other material having similar properties and characteristics) is molded so as to be positioned around first slug portion 74 and portion 44 of core distal portion 30.

Figure 9:
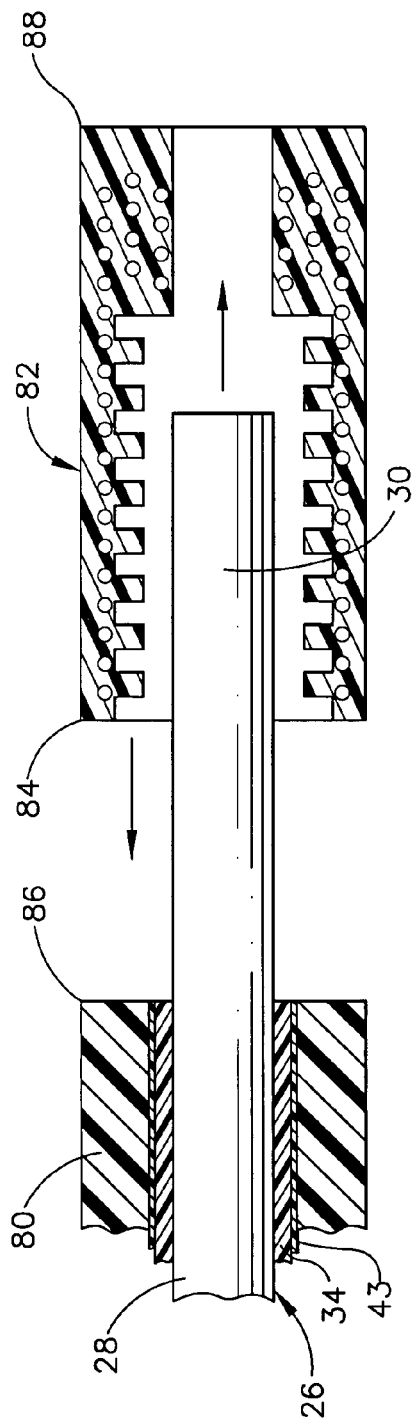
FIG. 9 is an enlarged, partial sectional view of a first alternative embodiment for the optical fiber depicted in FIGS. 1–3, where a tip diffuser is in a detached position and the penetrating tip has not been formed.
Figure 10:
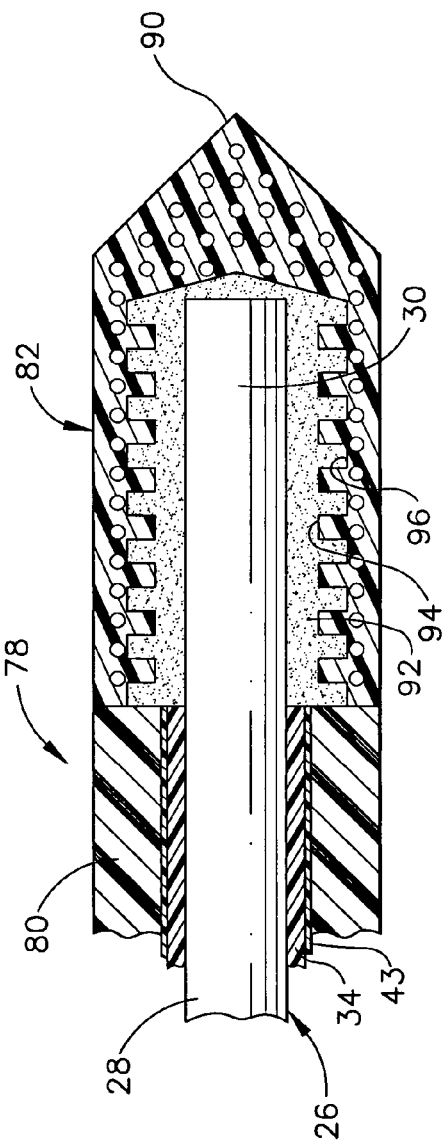
FIG. 10 is an enlarged, partial sectional view of the optical fiber depicted in FIG. 9, where the tip diffuser is in the attached position and the penetrating tip has been formed.

In a second embodiment of the optical fiber (identified generally by reference numeral 78), it will be seen from FIGS. 9 and 10 that slug 40 from FIGS. 2 and 3 has been eliminated. Further, while core 26, cladding layer 34, and buffer layer 43 remain unchanged, a sleeve 80 is provided which radially surrounds cladding layer 34 but not core distal portion 30. Accordingly, a tip diffuser 82 is provided which preferably surrounds core distal portion 30 and core distal face 32. In this way, the area of core 26 which receives the most treatment light also receives the most marker light excitation. Thus, the temperature measurement is weighted more closely to the tissue being treated.

As discussed previously herein with respect to slug 40, tip diffuser 82 preferably includes a light-scattering material (e.g., alexandrite or any other material having similar properties and characteristics) molded with substantially the same type of material utilized for sleeve 80. Tip diffuser 82 includes a first end 84 which is positioned adjacent a distal end 86 of sleeve 80 and a second end 88 which preferably is formed into a penetrating tip 90. It will be appreciated that first end 84 of tip diffuser 82 is preferably attached to sleeve distal end 86, such as by heat staking or welding.

A layer 92 of optical coupling material is preferably located between core distal portion 30 and tip diffuser 82. As seen in FIGS. 9 and 10, an interior surface 94 of tip diffuser 82 is preferably abraded to include grooves 96 or other variable surface characteristics so that a mechanical connection with optical coupling layer 92 is achieved and the disadvantage of index of refraction is overcome.

It will be appreciated that tip diffuser 82 is preferably a substantially homogeneous mixture of the light-scattering material and the material utilized for sleeve 80. Further, a preferred concentration of alexandrite in tip diffuser 82 exists and is dependent upon the configuration and composition of tip diffuser 82. In the case where tip diffuser 82 is a substantially homogeneous mixture of alexandrite and perfluoroalkoxy with approximately 10% barium sulfate, the preferred concentration of alexandrite therein is in a range of approximately 25–75%. It will be appreciated, however, that such concentration of alexandrite is likely to be less for tip diffuser 82 than for slug 40 described previously herein due to their respective orientations with regard to core distal portion 30.

FIG. 11 depicts a third embodiment of an optical fiber identified generally by reference numeral 98. Optical fiber 98 likewise includes core 26, buffer layer 43, and sleeve 80 as shown in FIGS. 9 and 10. A new tip diffuser 100 is utilized with optical fiber 98 which preferably is formed as a solid rod having a first end 102 positioned adjacent distal end 86 of sleeve 80 and a second end 104 which preferably terminates in a penetrating tip 106. It will be appreciated that first end 102 of tip diffuser 100 is preferably attached to sleeve distal end 86, such as by heat staking or welding.

Contrary to tip diffuser 82 of optical fiber 78, tip diffuser 100 has a smaller portion 107 hollowed therefrom at first end 102 so that only a portion 108 of core distal portion 30 extends therein. It will be noted that a cladding layer 110 radially surrounding core 26 extends into core distal portion 30 to core distal face 32. A layer 112 of optical coupling material is then preferably located between core distal face 32 and tip diffuser 100 to facilitate light emission from core distal portion 30. This particular configuration, where cladding layer 110 extends further on core 26, is effective for enhancing the flexibility of core distal portion 30 and thus rendering optical fiber 98 more compatible with certain flexible endoscopes.

Tip diffuser 100 preferably includes a light-scattering material (e.g., alexandrite or any other material having similar properties and characteristics) molded with substantially the same type of material utilized for sleeve 80. Once again, it will be appreciated that tip diffuser 100 is preferably a substantially homogeneous mixture of the light-scattering material and the material utilized for sleeve 80. Further, a preferred concentration of alexandrite in tip diffuser 100 exists and is dependent upon the configuration and composition thereof. When tip diffuser 100 is a substantially homogeneous mixture of alexandrite and perfluoroalkoxy with approximately 10% barium sulfate, the preferred concentration of alexandrite therein is in a range of approximately 25–75%. It will be appreciated, however, that such concentration of alexandrite is likely to be less for tip diffuser 100 than for slug 40 described previously herein due to their respective orientations with regard to core distal portion 30.

A fourth embodiment of an optical fiber 114 is depicted in FIG. 12. As seen therein, optical fiber 114 is configured to have core 26, cladding layer 34, buffer layer 43, and sleeve 80 as described above with respect to FIGS. 9 and 10. Another tip diffuser 116 is provided which preferably surrounds core distal portion 30 and core distal face 32. Further, tip diffuser 116 includes a first end 118 positioned adjacent distal end 86 of sleeve 80 and a second end 120 which preferably terminates in a penetrating tip 122. It will be appreciated that first end 118 of tip diffuser 116 is preferably attached to sleeve distal end 86, such as by heat staking or welding. It will be appreciated that an optical coupling layer 123 is shown as being provided between core distal portion 30 and tip diffuser 116.

More specifically, as seen in the upper portion of FIG. 12, tip diffuser 116 preferably includes a first substantially ring-shaped portion 124 which is sized to fit radially around a designated section 126 of core distal portion 30. Accordingly, first tip diffuser portion 124 is positioned axially at a middle section of core distal portion 30) along a longitudinal axis 133 through core distal portion 30. It is preferred in this embodiment that core distal portion 30 extend at least to a midpoint in tip diffuser 116 so that the temperature sensing ability of first tip diffuser portion 124 is enhanced by receiving the strongest light. In this configuration, first diffuser tip portion 124 includes a first end 127 (same as first end 118 of tip diffuser 116) which is attached to sleeve distal end 86 (e.g., by heat staking or welding) and a second end 128.

First diffuser tip portion 124 preferably consists of an exemplary light-scattering material (e.g., alexandrite or some other material exhibiting similar properties and characteristics) or a substantially homogeneous mixture of such light-scattering material and the material utilized for sleeve 80 (e.g., perfluoroalkoxy with barium sulfate particles or some material exhibiting similar properties and characteristics). Of course, a preferred concentration of alexandrite in first tip diffuser portion 124 exists and is dependent upon the configuration and composition thereof. When first tip diffuser portion 124 is a substantially homogeneous mixture of alexandrite and perfluoroalkoxy with approximately 10% barium sulfate, the preferred concentration of alexandrite therein is in a range of approximately 25–75%. It will be appreciated, however, that such concentration of alexandrite is likely to be less for first tip diffuser portion 124 than for slug 40 described previously herein due to their respective orientations with regard to core distal portion 30.

Tip diffuser 116 further includes a second portion 130 which preferably radially surrounds a second section 132 of core distal portion 30 and terminates in penetrating tip 122. Second tip diffuser portion 130, which preferably is composed essentially of the same material utilized for sleeve 80, includes an end 134 opposite penetrating tip 122 which is attached to second end 128 of first diffuser tip portion 124 (e.g., by heat staking or welding).

As seen in a bottom portion of FIG. 12, tip diffuser 116 may include a third substantially ring-shaped portion 136 which is sized to fit radially around an upstream or third section 138 of core distal portion 30. Third tip diffuser portion 136, which preferably consists essentially of the same type of material as sleeve 80, is located adjacent sleeve distal end 86A and includes a first end 140 (same as diffuser tip first end 118) and a second end 142 located opposite thereto. According, first end 140 of third diffuser section is attached to sleeve distal end 86A (e.g., by means of heat staking or welding) and second end 142 thereof is attached to first end 127 of first tip diffuser portion 124.

Figure 13:
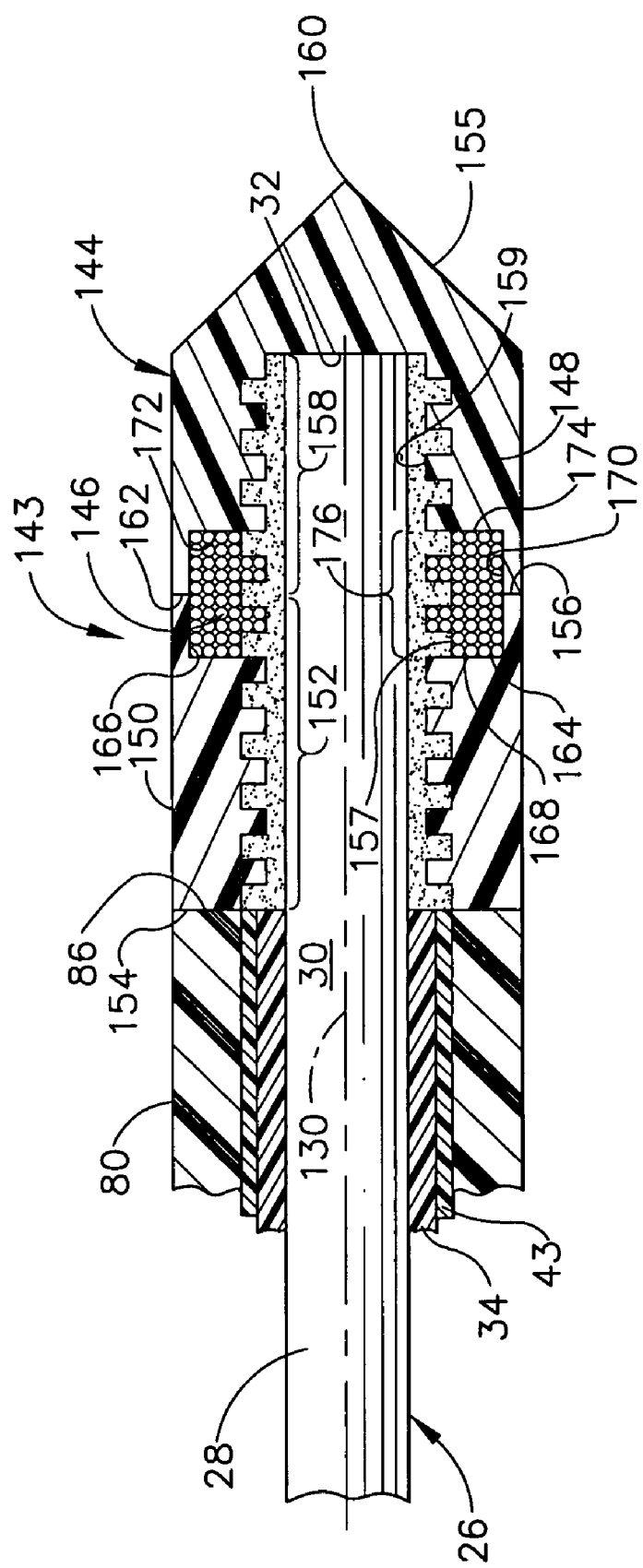

In yet another alternative optical fiber embodiment (represented by reference numeral 143) depicted in FIG. 13, it will be seen that a tip diffuser 144 includes a first tip diffuser portion 146, a second diffuser tip portion 148 and a third tip diffuser portion 150. As indicated above with respect to tip diffuser 116, third diffuser tip portion 150 is substantially ring-shaped, preferably consists essentially of the same type of material as sleeve 80, and is sized to fit radially around a third or upstream section 152 of core distal portion 30. Third diffuser tip portion 150 is located adjacent sleeve distal end 86 and includes a first end 154 and a second end 156 located opposite thereto.

Similarly, second diffuser tip portion 148 radially surrounds a second section 158 of core distal portion 30 and terminates in penetrating tip 160. Second tip diffuser portion 148, which preferably is composed essentially of the same material utilized for sleeve 80, includes an end 162 opposite penetrating tip 160 which is attached to second end 156 of third diffuser tip portion 146 (e.g., by heat staking or welding).

It will be noted that first tip diffuser portion 146 is preferably sized and configured so that a first end 164 and at least a portion thereof is received within, or otherwise mated with, a feature 166 formed in a middle section 168 of third tip diffuser portion second end 156. A similar feature 170 may be formed in a middle section 172 of second tip diffuser portion end 162 so that a second end 174 and at least a portion of first tip diffuser portion 146 is received therein or otherwise mated therewith. In particular, while features 166 and 170 are depicted as a female type, such features could alternatively have a male configuration which extends into complementary female portions formed in first and second ends 164 and 174, respectively, of first tip diffuser portion 146. In either case, first tip diffuser portion 146 will preferably radially surround a middle section 176 of core distal portion 30.

In conjunction with the optical fiber embodiments described herein, one improvement related thereto is the method of making and assembling such optical fibers. With respect to optical fiber 12, a method of making such optical fiber 12 includes an initial step of providing sleeve 42 radially around core 26 so that a length 178 of the open sleeve thereof extends beyond core distal face 32 a predetermined amount. The next step involves molding the light-scattering material with a material similar to that utilized for sleeve 42 to form slug 40, where the light-scattering material fluoresces in a temperature dependent manner upon being stimulated by light. Thereafter, slug 40 is inserted into open sleeve length 178 so as to be positioned adjacent core distal face 32. Open sleeve length 178 is then shaped into penetrating tip 64 having a predetermined geometry. It will be appreciated that slug 40 is also physically bonded to sleeve 42 during the tip shaping step. Also, it is preferred that optical coupling layer 36 be provided between core distal portion 30 and sleeve 42.

It will be understood with regard to the physical features of slug 40 that the method further may include the step of molding feature 46 at first end 48 of slug 40 for centering slug 40 with core distal portion 30. Another step may include the molding of negative feature 50 or positive feature 56 on second end 52 of slug 40 to facilitate placement of slug 40 on a corresponding assembly tooling 54 or 58, respectively, for the inserting step.

With respect to the materials utilized for slug 40, a preferred step is optimizing slug 40 with a predetermined concentration of the light-scattering material to the sleeve-type material utilized therewith. This can be different depending on the configuration and composition of slug 40. In a first instance, this involves the step of mixing the light-scattering material and the same type of material as utilized for sleeve 42 into a substantially homogeneous mixture prior to the molding step. For slug 66, the molding step further includes the steps of preloading the light-scattering material in a mold and compression molding the same type of material as utilized for sleeve 42 directly over and through the light-scattering material. The molding step for slug 72 further includes the following steps: mixing the light-scattering material and the same type of material as utilized for sleeve 42 into a substantially homogeneous mixture; molding first portion 74 of slug 72 with the mixture; and, molding second portion 76 of slug 72 from the same type of material as utilized for sleeve 42 so as to surround all but one side (that used to interface core distal face 32) of first slug portion 74.

Regarding optical fibers 78, 98, 114 and 143 shown in FIGS. 10, 11, 12, and 13 respectively, it will be understood that the process of making them involves the step of molding the light-scattering material with the same type of material utilized for sleeve 80 into at least a portion of tip diffusers 82, 100, 116, and 144, respectively, having a predetermined length and geometry. Thereafter, the respective tip diffuser 82, 100, 116 or 144 is inserted over at least a portion of core distal portion 30. The tip diffuser 82, 100, 116 or 144 is then attached at a first end 84, 102, 118, or 154, respectively, to distal end 86 of sleeve 80. Of course, the process also involves the step of forming penetrating tip 90, 106, 122 and 160 at second end 88, 104, 120, and 155, respectively, for each tip diffuser 82, 100, 116, and 144. The formation of penetrating tips 90, 106, 122 and 160 may occur prior to or after the inserting step described above.

It will be noted with respect to optical fibers 78, 114 and 143 that the method preferably includes the step of providing layers 92, 123, and 157, respectively, of optical coupling material between core distal portion 30 and tip diffusers 82, 116, and 143. In order to provide a desired physical or mechanical connection between optical coupling layers 92, 123, and 157 and interior surfaces 94, 125, and 159 of tip diffusers 82, 116, and 143, respectively, interior surfaces 94, 125, and 159 are preferably abraded prior to the inserting step. For optical fibers 78, 114, and 143, it will be seen that tip diffusers 82, 116, and 144 thereof extend around substantially all of core distal portion 30, whereas tip diffuser 100 of optical fiber 98 extends around only a small portion 108 of core distal portion 30.

With regard to the composition of tip diffusers 82 and 100, the process may further include the steps of mixing the light-scattering material and the same type of material utilized for sleeve 80 into a substantially homogeneous mixture and molding the mixture into such tip diffusers 82 and 100 having the predetermined length and geometry.

Regarding optical fibers 114 and 143, the process preferably includes the following additional steps: mixing the light-scattering material and the same type of material utilized for sleeve 80 into a substantially homogeneous mixture; molding first tip diffuser portions 124 and 146 from the mixture into a ring shape sized to radially surround sections 126 and 176 of core distal portion 30; and, molding second tip diffuser portions 130 and 148 from the same type of material utilized for sleeve 80 to surround sections 132 and 158. Additionally, such process preferably includes the step of attaching the respective first tip diffuser portions 124 and 146 and second tip diffuser portions 130 and 148 so as to have a common longitudinal axis 133 and 161 therethrough. Further steps may include forming penetrating tips 122 and 160 of predetermined geometry in second tip diffuser portions 130 and 148 and abrading interior surfaces 125 and 159 of tip diffusers 116 and 144.

Optionally, the process may include the step of molding third tip diffuser portions 138 and 150 from the same type of material utilized for sleeve 80 into a ring shape sized to radially surround sections 138 and 152 of core distal portion 30.

With respect to optical fiber 116, it will be appreciated that first tip diffuser portion 124 is preferably configured so that the method thereof includes attaching first end 126 to sleeve distal end 86 or to second end 142 of third tip diffuser portion 136 by heat staking or welding. In either case, second end 128 thereof is attached to non-penetrating tip end 134 of second tip diffuser portion 130 and 148, respectively.

With respect to optical fiber 143, the manner of attaching first tip diffuser portion 146 involves the steps of forming feature 166 in second end 156 of third tip diffuser portion 150 and/or forming feature 170 in end 162 of second tip diffuser portion 148. In this way, first tip diffuser portion 146 is mated with second and/or third tip diffuser portions 148 and 150.

Having shown and described the preferred embodiment of the present invention, further adaptations of optical fibers 12, 78, 98, and 114, including slugs 40, 66 and 72 and/or sleeves 42 and 80 thereof, as well as the methods making and assembling such optical fibers, can be accomplished by appropriate modifications by one of ordinary skill in the art without departing from the scope of the invention.

What is claimed is:

1. An optical fiber for use with a laser device including a source of light energy, said optical fiber having a proximal end adapted to be in communication with the light source and a diffuser portion positionable at a treatment site, said optical fiber comprising:
   (a) a core having a proximal portion, a distal portion and a distal face proximate said diffuser portion of said optical fiber;
   (b) a layer of cladding radially surrounding said core from said core proximal portion to a point adjacent said core distal portion;
   (c) a layer of optical coupling material radially surrounding at least a portion of said core distal portion;
   (d) a slug including a light-scattering material therein positioned adjacent said distal face of said core and a distal end of said optical coupling layer, wherein said light-scattering material fluoresces in a temperature dependent manner upon being stimulated by light; and,
   (e) a sleeve radially surrounding said cladding layer, said optical coupling layer and said slug, wherein said sleeve is composed essentially of a predetermined type of material;
wherein said light-scattering material of said slug is molded with substantially the same type of material utilized for said sleeve.

2. The optical fiber of claim 1, wherein said light-scattering material of said slug exhibits a temperature dependent optical fluorescence decay rate.

3. The optical fiber of claim 2, wherein said light-scattering material of said slug is alexandrite.

4. The optical fiber of claim 1, wherein said predetermined type of material used for said sleeve is a fluoropolymer.

5. The optical fiber of claim 4, wherein said sleeve material is perfluoroalkoxy impregnated with barium sulfate particles.

6. The optical fiber of claim 1, wherein a concentration of said light-scattering material to said sleeve type of material is in a range of approximately 25–75% by weight.

7. The optical fiber of claim 1, said slug being configured so as to radially surround a portion of said core distal portion.

8. The optical fiber of claim 1, wherein a mechanical connection is provided between said slug and said sleeve.

9. The optical fiber of claim 1, wherein said slug is a substantially homogeneous mixture of said light-scattering material and said sleeve type of material throughout.

10. The optical fiber of claim 1, said slug further comprising:
    (a) a first portion consisting essentially of said light-scattering material positioned adjacent said core distal face; and,
    (b) a second portion consisting essentially of said sleeve type of material positioned around said first slug portion and a portion of said core distal portion.

11. The optical fiber of claim 1, said slug further comprising:
    (a) a first portion consisting essentially of a mixture of said light-scattering material and said sleeve type of material positioned adjacent said core distal face; and,
    (b) a second portion consisting essentially of said sleeve material positioned around said first slug portion and a portion of said core distal portion.

12. The optical fiber of claim 1, wherein a first end of the slug is shaped to center said slug with respect to said core distal portion.

13. The optical fiber of claim 1, wherein a second end of said slug is shaped for interfacing with tooling utilized to position said slug with respect to said core.

14. The optical fiber of claim 1, wherein said optical coupling layer surrounds said slug.

* * * * *